United States Patent
Huang et al.

(10) Patent No.: US 9,284,565 B2
(45) Date of Patent: Mar. 15, 2016

(54) BACTERIAL EXPRESSION PLASMID

(75) Inventors: Ru Chih C. Huang, Baltimore, MD (US); Paul Edward Giza, Baltimore, MD (US)

(73) Assignee: The John Hopkins University, Baltimore, MD (US)

( * ) Notice: Subject to any disclaimer, the term of this patent is extended or adjusted under 35 U.S.C. 154(b) by 0 days.

(21) Appl. No.: 14/111,787

(22) PCT Filed: Apr. 13, 2012

(86) PCT No.: PCT/US2012/033502
§ 371 (c)(1),
(2), (4) Date: Nov. 15, 2013

(87) PCT Pub. No.: WO2012/142401
PCT Pub. Date: Oct. 18, 2012

(65) Prior Publication Data
US 2014/0065699 A1   Mar. 6, 2014

Related U.S. Application Data

(60) Provisional application No. 61/475,775, filed on Apr. 15, 2011.

(51) Int. Cl.
*C12N 15/71* (2006.01)
*C07K 14/245* (2006.01)
*C12N 15/62* (2006.01)
*C12N 15/70* (2006.01)

(52) U.S. Cl.
CPC .............. *C12N 15/71* (2013.01); *C07K 14/245* (2013.01); *C12N 15/62* (2013.01); *C12N 15/70* (2013.01)

(58) Field of Classification Search
None
See application file for complete search history.

(56) References Cited

U.S. PATENT DOCUMENTS

| 5,445,954 A * | 8/1995 | Huang et al. .............. 435/252.33 |
| 2001/0016351 A1 | 8/2001 | Sorge et al. |
| 2008/0248958 A1 | 10/2008 | Hollenbach |
| 2010/0021987 A1 | 1/2010 | Zuo et al. |

FOREIGN PATENT DOCUMENTS

WO   89-07141 A1   8/1989

OTHER PUBLICATIONS

Giza, et al., "A self-inducing runaway-replication plasmid expression system utilizing the Rop protein", Gene, vol. 78 (1), pp. 73-84 (May 15, 1989).

* cited by examiner

*Primary Examiner* — Nashaat Nashed
(74) *Attorney, Agent, or Firm* — John Hopkins Technology Transfer

(57) ABSTRACT

The present invention provides expression vectors useful for high-throughput screening of gene libraries. In a specific embodiment, an expression vector comprising (a) the Rop gene operatively linked to the trp promoter-operator; (b) a purification tag sequence and a protease cleavage site downstream of the Rop gene; and (d) a multiple cloning site downstream of the protease cleavage site, wherein the insertion of a heterologous gene of interest into the multiple cloning site and subsequent expression thereof in a host cell produces a high yield of a fusion protein comprising the Rop protein and the protein encoded by the heterologous gene of interest without the need of chemical inducers, temperature shifts, or growth medium alterations to initiate protein synthesis, and wherein the fusion protein controls plasmid replication at temperatures below about 30° C. but exhibits runaway plasmid replication when cultured at about 37° C.

17 Claims, 3 Drawing Sheets

```
                                    pPGtrpRop63
         50            60            63                    70
LeuTyrArgSerCysLeuAlaArgPheGlyAspAspGlyAsnLeuArgSerHisHisHisHis
CTTTACCGCAGTGTCTGCGCACGTTTCGGGGATGACGGTGAAAACCTGAGATCCCACCATCACCATCAC
             Thrombin         80                   87
HisArgSerLeuValProArgGlyThrProGlyIleSerAlaAspLeuAspStp  (SEQ ID NO:1)
CATAGATCTCTGGTTCCGCGTGGTACCCCGGGATATCAGCTGATCTAGATTAGTATCTGCCTCGC..(SEQ ID NO:2)
 BglII        KpnI   SmaI EcoRV PvuII
                          XmaI KpnI        PvuII
     1/2 site     1/2 site
        CCCCGGGGGATCCAG    (SEQ ID NO:3)            Reading frame A
        CATGGGGCCCCTAGGTC  (SEQ ID NO:4)
            SmaI  BamHI CCCCGGGGATCCAG    (SEQ ID NO:5)            Reading frame B
         CATGGGGCCCCTAGGTC (SEQ ID NO:6)
             SmaI BamHI CCCCGGGGATCCAG    (SEQ ID NO:7)           Reading frame C
          CATGGGGCCCCTAGGTC (SEQ ID NO:8)
              SmaI BamHI pPGtrpRop63BamHI A,B,C

FIG. 1
```

BACTERIAL EXPRESSION PLASMID

CROSS-REFERENCE TO RELATED APPLICATIONS

This application is a 35 U.S.C. §371 U.S. national entry of International Application PCT/US2012/033502 having an international filing date of Apr. 13, 2012, which claims the benefit of U.S. Provisional Application No. 61/475,775 filed Apr. 15, 2011, the content of each of the aforementioned applications is herein incorporated by reference in their entirety.

FIELD OF THE INVENTION

The present invention relates to the field of expression vectors. More specifically, the present invention provides expression vectors useful for high-throughput screening of gene libraries.

INCORPORATION-BY-REFERENCE OF MATERIAL SUBMITTED ELECTRONICALLY

This application contains a sequence listing. It has been submitted electronically via EFS-Web as an ASCII text file entitled "P10467-03_ST25.txt" The sequence listing is 4,384 bytes in size, and was created on Apr. 11, 2012. It is hereby incorporated by reference in its entirety.

BACKGROUND OF THE INVENTION

Technical advances in the sequencing of DNA have led to the sequencing of numerous genomes from simple bacteria to complex eukaryotic genomes, including humans. Great advances have also been realized in the ever expanding field of proteomics, which is involved with the identification, expression, structure, and function of proteins produced by the genome.

The past decade has seen rapid development in the field with the expansion in the use of microarrays to analyze protein expression and abundance. The clinical area of proteomic research has been greatly advanced by the use of two-dimensional gel electrophoresis combined with mass spectroscopic sequencing to analyze protein expression in pathogenic microorganisms and to identify protein targets for cancer therapy.

Functional proteomics' ultimate goal is to determine what each protein in an organism does, how it does it, and examine the myriad of conditions that influence its activity. To accomplish this task, proteins must be either purified from their natural environment or produced using recombinant DNA technology—the only practical method to achieve this goal.

During the past several years methods have been developed for the cloning of PCR generated open reading frame (ORF) libraries in bacterial entry vectors that could be transferred to a variety of expression vectors (destination, vectors) using site specific recombination technology that maintains the proper reading frame and gene orientation. The incorporation of affinity tags is usually required during plasmid construction to facilitate purification and concentration of the target proteins. Scoring of positive results is initially performed on standard Coomassie stained protein gels or Western blots after high-throughput purification using robotic platforms.

Numerous expression systems could be used for high-throughput, robotic production and purification of recombinant proteins using a variety of prokaryotic and eukaryotic inducible vectors and hosts. All of these systems rely on tight regulation of transcription during logarithmic phase of growth followed by chemical, induction to initiate protein production. There is a great need for the development of expression systems that are more adaptable for large-scale culture and also suitable for use as a high-throughput vector.

SUMMARY OF THE INVENTION

The present invention is based, at least in part, on the development of a bacterial expression plasmid that produces fusion proteins with average yields of more than about 300 micrograms per milliliter of culture without the need of chemical, inducers or temperature shifts to initiate protein synthesis. The high yields were obtained with culture volumes as small as 100 microliters or as large as several liters with the inoculums being a single colony, overnight seed culture or frozen glycerol stocks. The plasmid carries the rop gene which encodes the 63 amino acid flop protein. This protein plays the dual role of being the fusion partner and the controller of plasmid copy number. Fusion, proteins are capable of controlling plasmid replication at temperatures below 30° C., but completely lose this ability when cells are cultivated at 37° C. During early stationary phase of induction growth, fusion plasmid DNA accumulates to high levels leading to the titration of the genomically produced tryptophan repressor molecules and induction of the tryptophan promoter situated upstream of the top gene and promoter. An analysis of more than 150 clones obtained by the ligation of random DNA fragments at the 3' end of the rop coding sequence results in easily observable novel bands (96% positive) when 1 microliter of culture, grown, in 150 microliters of broth in 96-well plates was applied to standard protein, gels. The present inventors also describe the overproduction of 8 proteins ranging in size from 61 to 288 amino acids with purified yields of about 70 to about 1,300 micograms per milliliter of induced culture.

The present inventors previously have developed a bacterial expression system that produced large amounts of fusion proteins using the rop gene as the fusion partner and the tryptophan (trp) promoter as the transcription enhancer. See Giza and Huang, 78 GENE 73-84 (1989). This system, required no exogenous chemical inducers, temperature shifts, or growth medium alterations to initiate protein synthesis. However, the system required the use of 2 similar plasmids co-residing in the cell, making it user friendly for large cultures, but intractable for use in high-throughput methodology. The present inventors have modified the expression plasmid and have not only made it more adaptable for large-scale cultures but also have made it extremely suitable for use as a high-throughput vector that eliminates several of the steps that current vectors require for cost efficient high-throughput screening of gene libraries.

Accordingly, in one aspect, the present invention provides expression vectors for producing high proteins yields. In one embodiment, an expression vector comprises a nucleic acid sequence encoding (a) the trp promoter-operator; (b) the Rop promoter and Rop gene downstream from the trp promoter-operator; (c) a purification tag sequence and a protease cleavage site downstream of the Rop promoter and Rop gene; and (d) a multiple cloning site downstream of the protease cleavage site. In a specific embodiment, the purification tag sequence is a polyhistidine tag sequence. In another embodiment, the Rop gene encodes the amino acid sequence of SEQ ID NO: 12. In a more specific embodiment, the Rop gene encodes a polypeptide having at least about 95% identity to SEQ ID NO: 12. In a further embodiment, the protease is thrombin.

In a specific embodiment, a recombinant expression vector comprises a nucleic acid sequence encoding (a) the trp promoter-operator; (b) the Rop promoter and Rop gene downstream from the trp promoter-operator; (c) a polyhistidine tag sequence and a thrombin cleavage site downstream of the Rop promoter and Rop gene; and (d) a multiple cloning site downstream of the protease cleavage site. In certain embodiments, the Rop gene encodes the amino acid sequence of SEQ ID NO: 12. In a specific embodiment, the Rop gene encodes a polypeptide having at least about 95% identity to SEQ ID NO: 12.

In particular embodiments, the present invention provides a recombinant bacterial expression vector comprising (a) the trp promoter-operator; (b) a the Rop promoter and Rop gene positioned 3' to the trp promoter-operator; (c) a purification tag sequence and a protease cleavage site positioned 3' to the Rop promoter and Rop gene; and (d) a multiple cloning site positioned 3' of the protease cleavage site. The tag sequence can be a polyhistidine tag sequence. In a specific embodiment, the Rop gene encodes the amino acid sequence of SEQ ID NO: 12. In a more specific embodiment, the Rop gene encodes a polypeptide having at least about 95% identity to SEQ ID NO: 12. In yet another embodiment, the protease is thrombin.

The present invention also provides a plasmid designated pPGtrpRop$_{63}$. In another embodiment, the present invention provides a plasmid designated pPGtrpRop$_{63}$BamHI A, B, C. In certain embodiments, a prokaryotic cell line comprises plasmid described herein, in particular embodiments, the cell line is a bacterial cell line. In specific embodiments, the bacterial cell line is an *E. coli* cell line.

In another aspect, the present invention provides kits useful for producing high yields of a protein of interest. Specifically, a kit can comprise an expression vector or a plasmid described herein.

In yet another aspect, the present invention provides art expression cassette. In one embodiment, an expression cassette comprises the Rop gene operatively linked to the trp promoter-operator, in another embodiment, a plasmid comprises an expression cassette described herein. In one embodiment, the Rop gene encodes the amino acid sequence of SEQ ID NO: 12. In a more specific embodiment, the Rop gene encodes a polypeptide having at least about 95% identity to SEQ ID NO: 12.

In another embodiment, the expression cassette further comprises (a) a purification tag sequence; (b) a protease cleavage site; and (c) a multiple cloning site, wherein the insertion of a heterologous gene of interest into the multiple cloning site and subsequent expression thereof in a host cell produces a high yield of a fusion protein comprising the Rop protein and the protein encoded by the heterologous gene of interest.

In yet another embodiment, the plasmid further comprises (a) a purification tag sequence; (b) a protease cleavage site; and (c) a multiple cloning site, wherein the insertion of a heterologous gene of interest into the multiple cloning site and subsequent expression thereof in a host cell produces a high yield of a fusion protein comprising the Rop protein and the protein encoded by the heterologous gene of interest.

In certain embodiments, an expression vector comprises the Rop gene operatively linked to a negatively controlled promoter-operator (e.g., trp, lac, etc.) and produces high yields of fusion proteins comprising the Rop protein and protein of interest. In particular embodiments, the Rop portion of the fusion protein can be cleaved from the protein of interest using, for example, a protease that cleaves at a particular site. The expression, vector can further comprise a purification tag sequence to purify the fusion protein from culture. Any appropriate sequence can be used including, for example, a polyhistidine tag sequence.

In particular embodiments, an expression vector comprises (a) the Rop gene operatively linked to the trp promoter-operator; (b) a purification tag sequence and a protease cleavage site downstream of the Rop gene; and (d) a multiple cloning site downstream of the protease cleavage site, wherein the insertion of a heterologous gene of interest into the multiple cloning site and subsequent expression thereof in a host cell produces a high yield of a fusion protein comprising the Rop protein and the protein encoded by the heterologous gene of interest without the need of chemical inducers, temperature shifts, or growth medium alterations to initiate protein synthesis, and wherein, the fusion protein controls plasmid replication at temperatures below about 30° C. but exhibits runaway plasmid replication when cultured at about 37° C. In certain embodiments, a host cell comprises an expression vector described herein.

BRIEF DESCRIPTION OF THE FIGURES

FIG. 1 shows the sequence of the expression vectors at the terminus of the rop gene. The vector pPGtrpRop$_{63}$ was produced by the insertion of the underlined sequence at the PvuII site (CAG/CTG) of the plasmid pPGtrpRopAp. See Giza and Huang, 78 GENE 73-84 (1989). The underlined sequence was modified by the replacement of the KpnI-PvuII fragment with 3 adapters to produce vectors with BamHI sites in 3 reading frames. Numbers denote the amino acid sequence of the protein produced, by pPGtrpRop$_{63}$ with amino acid 63 being the carboxy-terminus of the Rop protein. The thrombin cleavage sequence is LeuValProArg/GlyThr. (SEQ ID NO:9)

FIG. 2A: frozen glycerol stocks were inoculated in 20 ml of LB medium and cultivated at 25° C. for 18 hours. Lanes 1-8; IN, GFP, Sp1, Surv, ICAM, Tat, gp41, MT. FIG. 2B": same fusion constructs as (A) except cells were grown in TB and cultivated at 37° C. for 18 hours. FIG. 2C: fresh overnight cultures (grown at 25° C.) inoculated in 20 ml of TB (500-fold dilution) and incubated at 3° C. for 18 hours. Lanes 1-7; IN, GFP, Sp1, Surv, ICAM, gp41, MT. Lanes to the right of numbered lanes were loaded with 3 μg of protein eluted from a HiTrap Chelating HP column (Amersham Pharmacia Biotech) as described in Methods. Lanes marked V denote vector without insert.

FIG. 3A: lanes 1-8 were loaded with 0.5 μL of induced cultures that were incubated at 37° C. in 96 well plates in the order IN, GFP. Sp1, Surv, ICAM, Tat, gp41, MT. FIG. 3B: randomly selected colonies from shotgun ligation inoculated and grown under the same conditions as FIG. 3A. FIG. 3C: bulk mixed colonies grown in liquid culture and on agar plates. Liquid: lane 1, non-induced (25° C.) total proteins; lane 2, column eluate (non-induced); lane 3, induced (37° C.) total proteins; lane 4, column flow-through of lane 3 proteins; lane 5, column eluate (induced); lane 6, same as 5 except 4-fold more; lane 7, thrombin digest of proteins in lane 6; Plate: lanes 1-4, total proteins (non-induced); column eluate (non induced); total proteins from ~1,200 colonies (induced); column eluate (induced). Lanes marked V denote vector without insert grown under induced conditions.

Figure 2:
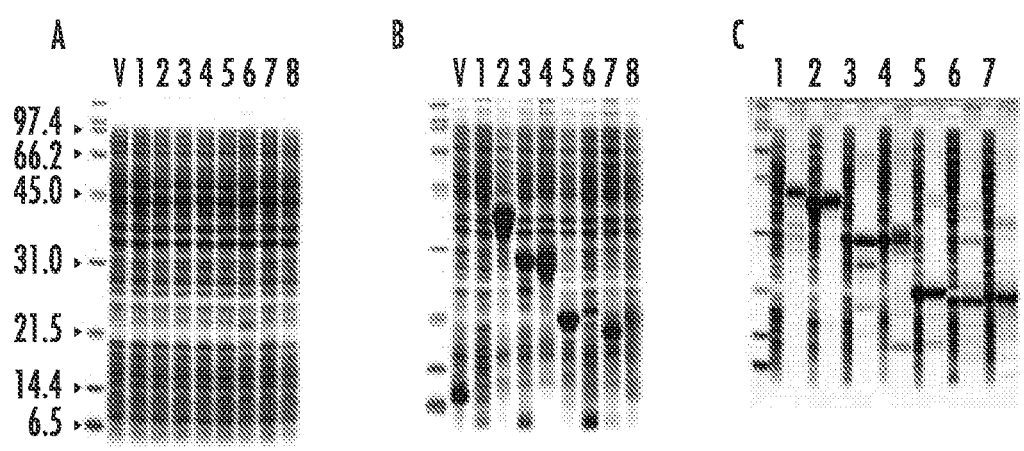
FIG. 2 shows a 14% SDS-PAGE of temperature dependent expression of rop gene fusions in the vector pPGtrpRop$_{63}$.

Plasmid pPGtrpRop$_{63}$ was deposited Sept. 11, 2015, under terms of the Budapest Treaty with the American Type Culture Collection (ATCC®), 10801 University Blvd., Manassas, VA 20110, and given designation number PTA-122515. Plasmid pPGtrpRop$_{63}$BamHIA was deposited Sept. 11, 2015, under terms of the Budapest Treaty with the American Type Culture Collection (ATCC®),10801 University Blvd., Manassas, VA 20110, and given designation number PTA-122516. pPGtrpRop$_{63}$BamHIB was deposited Sept. 11, 2015, under terms of the Budapest Treaty with the American Type Culture Collection (ATCC®), 10801 University Blvd., Manassas, VA 20110, and given designation number PTA-122517. pPGtrpRop$_{63}$BamHIC was deposited Sept. 11, 2015, under terms of the Budapest Treaty with the American Type Culture Collection (ATCC®), 10801 University Blvd., Manassas, VA 20110, and given designation number PTA-122514.

DETAILED DESCRIPTION OF THE INVENTION

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited, herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

The term "fusion" or "hybrid" protein, DMA molecule, or gene refers to a chimera of at least two covalently bonded polypeptides or DNA molecules The term, "nucleic acid" or "polynucleotide" refers to a polymeric form of nucleotides of any length, either ribonucleotides and/or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the nucleic acid can comprise sugars and phosphate groups (as may typically be found in RNA or DNA), or modified, or substituted sugar or phosphate groups. Alternatively, the backbone of the nucleic acid can comprise a polymer of synthetic subunits such as phosphoramidates and thus can be an oligodeoxynucleoside phosphoramidate (P—NH$_2$) or a mixed phosphoramidate-phosphodiester oligomer. In addition, a double-stranded nucleic acid can be obtained from the single stranded nucleic acid product of chemical synthesis either by synthesizing the complementary strand and annealing the strands under appropriate conditions, or by synthesizing the complementary strand de novo using a DNA polymerase with an appropriate primer.

The following are non-limiting examples of nucleic acids: a gene or gene fragment, exons, introns, mRNA, tRNA, rRNA, ribozymes, cDNA, recombinant nucleic acids, branched nucleic acids, plasmids, vectors, isolated DNA of any sequence, isolated RNA of any sequence, nucleic acid probes, and primers. A nucleic acid may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A nucleic acid may be further modified after polymerization, such as by conjugation with a labeling component. Other types of modifications included in this definition are caps, substitution of one or more of the naturally occurring nucleotides with an analog, and introduction, of means for attaching the nucleic acid to proteins, metal ions, labeling components, other nucleic acids, or a solid support.

As used herein, the term "operably linked" means that nucleic acid sequences or proteins are operably linked when placed into a functional relationship with another nucleic acid sequence or protein. For example, a promoter sequence is operably linked to a coding sequence if the promoter promotes transcription of the coding sequence. As a further example, a repressor protein and a nucleic acid sequence are operably linked if the repressor protein binds to the nucleic acid sequence. Additionally, a protein may be operably linked to a first and a second nucleic acid sequence if the protein binds to the first nucleic acid sequence and so influences transcription of the second, separate nucleic acid sequence. Generally, "operably linked" means that the DNA sequences being linked are contiguous, although they need not be, and that a gene and a regulatory sequence or sequences (e.g., a promoter) are connected in such a way as to permit gene expression when the appropriate molecules (e.g., transcriptional activator proteins—transcription factors—or proteins which include transcriptional activator domains) are bound to the regulatory sequence or sequences.

The term "plasmid" refers to an extrachromosomal circular DNA capable of autonomous replication in a given cell. In certain embodiments, the plasmid is designed for amplification and expression in bacteria. Plasmids can be engineered by standard molecular biology techniques. See Sambrook et al. Laboratory Manual, Cold Spring Harbor Laboratory Press, Cold Spring Harbor (1989), N.Y. The term "expression vector" is used interchangeably herein with the term "plasmid" and refers to a recombinant DNA molecule containing a desired coding sequence and appropriate nucleic acid sequences necessary for expression of the operably linked coding sequence (e.g. an insert sequence that codes for a product) in a particular host cell. Nucleic acid sequences necessary for expression in prokaryotes usually include a promoter, an operator (optional), and a ribosome binding site, often along with other sequences.

The term "promoter" refers to the DNA region, usually upstream of the coding sequence of a gene or operon, which binds RNA polymerase and directs the enzyme to the correct transcriptional start she. Some embodiments of the present invention contemplate the use of promoters which contain at least one operator associated with a promoter sequence. The operator is positioned such that the binding of a repressor to the operator represses transcription from the promoter. Operators are well known in the art and include, for example, the tryptophan operator of the tryptophan operon of *E. coli*. The tryptophan repressor, when bound to two molecules of tryptophan, binds to the *E. coli* tryptophan operator and, when suitably positioned (i.e., operatively linked) with respect to the promoter, blocks transcription. Thus, in particular embodiments, the terms "trp promoter" and "trp promoter-operator" can be used interchangeably to refer to a regulatory sequence comprising a trp promoter and a trp operator.

Additional examples of operators which can be used with the invention include the Lac operator and the operator of the molybdate transport operator/promoter system of E. coli. Other operators can include, but are not limited to, the xylose operator ("xylO"), the tetracycline operator ("tetO"), the maltose operator ("malO"), and the lambda Cl operator ("λclO"). These operators can be induced by the following inducers, respectively: xylose or analog thereof, tetracycline or analog thereof, maltose or analog thereof, lactose or analog thereof, tryptophan or analog thereof and temperature.

The terms "restriction endonuclease" and "restriction, enzyme" refer to enzymes (e.g. bacterial enzymes), each of which cut double-stranded DNA at or near a specific nucleotide sequence (a cognate restriction site). Examples include, but are not limited to, BamHI, EcoRV, HindIII, HincII, NcoI, SalI, and NotI. The term "restriction" means cleavage of DNA by a restriction enzyme at its cognate restriction site. The term "restriction site" refers to a particular DNA sequence recognized by its cognate restriction endonuclease.

As used herein, the term "ROP gene" refers to a gene encoding the repressor of primer protein, which regulates plasmid DNA replication by modulating the initiation of transcription. Rop is a 7.2-kDa, 63 amino acid plasmid-encoded protein, which acts in concert with RNA 1 to negatively regulate copy number in some ColE1 and ColE1-like plasmids. In certain embodiments, the term "Rop gene" refers to a nucleic acid sequence that encodes the amino acid sequence of SEQ ID NO: 12. In other embodiments, the term "Rop gene" includes nucleic acid sequences that encodes a Rop polypeptide having at least about 90%, at least about 91%, at bast about 92%, at least about 93%, at least about 94%, at least about 95%, at least about 96%, at least about 97%, at least about 98%, at least about 99% or more sequence identity to SEQ ID NO: 12.

As used herein, a "selectable marker" refers to a phenotypic trait conferred on transformed cells that protects them from a selective agent in their environment, i.e., the growth media. Examples of selectable markers include, but are not limited to, antibiotic resistance markers (e.g., genes encoding resistance to kanamycin, ampicillin, chloramphenicol, gentamycin, or tetracycline) and metabolic markers (e.g., amino acid synthesis genes or transfer RNA genes).

As used herein, the term "vector" refers to a nucleic acid construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell. The term "replication" means duplication of a vector.

The expression plasmid described, herein produces fusion proteins at yields of greater than about 300 μg/ml of culture whether cultivated on milliliter or liter scales. These yields were realized without the need of chemical inducers, culture modifications, or temperature shifts during growth. Culture growth could be initiated with the inoculum being a single colony, overnight culture, or glycerol stock culture. The system is applicable to high-throughput processing as well as large scale production.

This system is successful at producing high protein yields because of the combination of high culture densities at laboratory scale production, and high cellular protein concentrations due to proteins accumulating as IBs. Because IBs are quite resistant to degradation, they can accumulate during prolonged incubation after initiation of protein synthesis. Many expression systems produce IBs, or a mixture of IBs and soluble protein, and methods have been published to differentiate these species using high-throughput processing. However, the problem with IBs is not the serious issue it was a decade ago. Numerous methods have been developed for the denaturation and refolding of IBs into functional proteins on a laboratory as well as industrial scale. In the area of high-throughput analysis of expression, the formation of IBs are looked upon as an advantage in this system, because their formation is responsible for the greater than 95% success rate described herein. Also, the early stages of expression analysis require solubilization and denaturation of proteins prior to SDS-PAGE analysis and Western blotting, so the insolubility status of the target protein is irrelevant, at least initially.

To compare the expression plasmid of the present invention with other systems, the present inventors relied heavily upon the work conducted by The Institute of Proteomics, Harvard Medical School and other institutions, who have tested and compared a number of commercial vectors in their ability to produce recombinant proteins from ORF libraries that could be analyzed in large numbers using robotic, high-throughput processing. See Hu et al, 17 GENOME RES. 536-43 (2007); Aguiar et al. 14 GENOME RES. 2076-82 (2004); Marsischky and LaBaer, 14 GENOME RES. 2020-28 (2004); Murthy et al., 36 PROTEIN EXPR. PURIF. 217-225 (2004); Braun et al, 99 PROC NALT. ACAD. $S_{CI}$. U.S.A. 2654-59 (2001); and Büssow et al, 65 GENOMICS 1-8 (2000). The processing methodology was the same in all cases. Colonies were robotically picked and grown in 96 well plates overnight followed by inoculation and growth in fresh medium, (usually 1 ml). The cultures were monitored, and a chemical inducer was added (usually IPTG) at an appropriate culture density. After induction growth of several hours, cells were harvested and stored, or the target proteins were purified by high-throughput processing using the appropriate purification matrix. Purification of proteins was usually required because insufficient amount of protein were produced to be unambiguously identified on protein gels except when total proteins were applied to gels followed by Western blot analysis.

After induction growth, the success rate at seeing novel bands was in the range of about 60 to about 85% with the various systems alter applying total proteins to gels from 5 to 10 μL of culture followed by Western blot analysis. Affinity purified samples were analyzed by SDS-PAGE using about 50 to about 150 μL of culture. The fusion protein yields ranged from about 0.3 to more than about 1 μg per well. Plasmid yields were not given for the various systems, but in general most expression systems are engineered to keep plasmids levels low so that they do not titrate the repressors that control transcript ion.

Rather than suppressing plasmid levels, the present inventors used runaway plasmid replication to automatically induce transcription at 37° C. dining late growth phase after culture densities have reached levels approaching about 20 $OD_{600}$ in a few cases. Thermal induction is not new, but it is usually done at temperatures between 40 and 45° C.; temperatures not very optimum for growth and health of the host bacteria. After induction growth in 96 well plates using 150 μL of media, novel hands were easily observed using 0.5 to 1.5 μL of culture without fusion protein purification or Western blots. The protein yields per well ranged from about 15 to about 70 μg compared to the other systems that produced, levels of 0.3 to 1 μg per well using 6-fold more culture volume. Plasmid DNA levels averaged about 1.3 μg per well providing sufficient DNA for restriction digests. Larger induced culture volumes (1 ml) could provide sufficient, plasmid yields for sequencing.

Larger scale inductions of 1 to 2 liters produced yields per volume comparable to smaller inductions. In the case of cells harboring pRop$_{63}$Sp1$_{156}$, a 1.5 liter preparation produced about 800 mg of column pure RopSp1-fusion (533 mg/L) or about 530 mg of target Sp1 protein (353 mg/L) using a standard laboratory shaker. This sort of yield falls within the range of some protein yields produced by commercial vectors that rely upon high density fermentation that produce culture densities of 50-80 OD$_{600}$ units. See Achmüller et al., 4 NAT. METHODS 1.037-43 (2007); Sharma et al., 125 J. BIOTECHNOL, 48-56 (2006); and Terpe et al, 72 APPL. MICROBIOL. BIOTECHNOL, 211-22 (2006).

In conclusion, the expression system of the present invention can be used to produce fusion proteins at high yields on a large or small scale and is very suitable for use in high-throughput expression analysis, because it bypasses several of the steps required using other commercial vectors. The vector could be easily converted to a destination vector using, for example, Gateway Technology (Invitrogen) for non-ligation recombination cloning of available ORF libraries that have been cloned into Gateway entry vectors. The combination of high yields of target proteins, efficient purification and protease cleavage capabilities, ease of use, and low cost when used in high-throughput or larger scale protein production make this vector an attractive alternative to the arsenal of vectors currently used in functional proteomic research.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Construction of Expression Vector pPGtrpRop$_{63}$. This vector was derived from the vector pPGtrpRopAp whose construction has been described in detail (Giza and Huang 1989). The single EcoRV site located down-stream from the trp promoter was eliminated by digestion of the plasmid with EcoRV followed by transformation and plasmid extraction of the transformation culture. The digestion was repeated and transformed cells were plated for colonies. Colonies were screened for plasmids that lacked the EcoRV site. Additional modifications were made as described in FIG. 1.

Construction of Library Expression Vectors pPGtrpRop$_{63}$BamHI A, B, C. The vector pPGtrpRop$_{63}$ carries a single BamHI site downstream from the trp promoter. This site was eliminated by digestion of the plasmid with BamHI, filling-in the ends, religating, transforming, and screening colonies lacking a BamHI site. The resultant plasmid was digested with PvuII and modified by the insertion of the 115 bp sequence shown in FIG. 1. The original PvuII site in the rop coding sequence was eliminated resulting in codon changes for Ser$_{51}$ (AGC to AGT) and Cys$_{52}$ (TGC to TGT).

Construction of 8 Rop Gene Fusion Plasmids. All of these constructs were made in the vector pPGtrpRop$_{63}$. The subscripts following the gene designation indicate the number of amino acids in the target protein. The HIV-1 integrase (IN) gene was excised from the plasmid pINSD.His.Sol (Jenkins et al. 1996) by digestion with NdeI+BamHI, filled-in, and ligated to the vector at the EcoRV site to produce pRop$_{63}$IN$_{288}$. The plasmid pEGFP-N3 (BD Bioscience Clonetech) was digested with NcoI+XbaI and the fragment carrying the entire green fluorescent protein gene (GFP) was filled-in and ligated at the EcoRV site to produce pRop$_{63}$GFP$_{239}$. The plasmid Sp1-167C (Sjøttem et al. 1997) was digested with Sau3AI, filled-in, and a 469 bp fragment was ligated to the vector at the SmaI site. The fragment spans the entire 3 zinc-finger domains of Sp1 plus an additional 68 amino acids down-stream to produce pRop$_{63}$Sp1$_{156}$. The plasmid survivin pcDNA3.1-myc-His (Chang et al. 2004) was used as the template with the primers 5' CATCCCGG-GATGGGAGCTCCGGCGCTGCCC (SEQ ID NO:10) and 5' TACCCCGGGTTAGGCAGCCAGCTGCTCAATTGA (SEQ ID NO:11) to generate a PGR product that encoded the entire murine survivin gene (Surv) with XmaI restriction site termini. The fragment was ligated at the XmaI site to produce pRop$_{63}$Surv$_{140}$. A 277 bp PGR generated fragment with BamHI ends (kindly provided by Molecular Therapeutics Inc. West Haven, Conn.) was filled-in and ligated at the SmaI site. The fragment carries the coding region for 88 amino acids of the N-terminal domain of ICAM-1 (Stanton et al. 1988) to produce pRop$_{63}$ICAM$_{88}$. The HIV-1 envelope gene, strain BH10 (Mudrow et al 1987), was digested with StyI and a 268 bp fragment was filled-in and ligated at the SmaI site. The fragment encodes 90 amino acids of residues 520 to 609 (Chan et al 1997) and was designated pRop$_{63}$gp41$_{90}$. The entire HIV-1 tat gene was removed from the plasmid pRop-Tat (Giza and Huang 1989) by digestion with PvuII and ligated at the EcoRV site to produce pRop$_{63}$Tat$_{86}$. A DNA restriction fragment carrying the entire Chinese hamster metallothiomm gene (MT) with ClaI linkers (Giza and Huang 1989) was ligated to the vector at the PvuII site to produce pRop$_{63}$MT$_{61}$.

Construction of Test Expression Library. High molecular weight E. coli DNA was digested with Sau3AI and fragments were separated on 1% agarose gels. Fragment sizes from 100-400 bp and 300-600 bp were excised from the gels and purified using QIAEX II Gel Extraction Kit (QIAGEN Science). Vectors pPGtrpRop$_{63}$BamHI A, B, and C were digested with BamHI, phosphatased, and purified on agarose gels to eliminate any circular plasmid and non-vector DNA from contaminating the ligation reactions. Ligations were performed using 150 ng of each vector and 1, 2, and 3 molar excess of the fragments in 20 µL reaction volumes incubated at 16° C. for 18 hours.

Transformation and Cultivation of Fusion Clones Under Non-Induced Conditions. The host HB101 was used in all experiments. Bacteria were grown in LB medium (Sambrook et al. 1989) at 37° C. to an OD$_{600}$ of about 0.8, centrifuged and made competent by incubation on ice in 100 mM CaCl$_2$. DNA was added and cells were incubated on ice for 1 hour followed by a heat shock at 45° C. for 45 seconds. The cells were diluted 10-fold with LB broth and incubated for 1 hour at 37° C. A portion of the culture was spread on LB plates to determine the number of transformants, and the remainder was diluted 100-fold in LB broth and allowed to grow to saturation at room temperature.

Cultivation of Fusion Clones Under Induced Conditions in Liquid Media. Terrific Broth (TB) (Sambrook et at), supplemented with 200 μg/ml ampicillin (Ap) was used in all induction experiments. Media was inoculated with single colonies, frozen glycerol stocks, fresh overnight room temperature cultures, or in some cases transformation reactions. Best results were usually obtained with fresh stock cultures because incubation times could be more accurately determined and culture densities were generally higher. All cultures were induced at 37° C. In some cases higher yields were obtained at growth temperatures between 30 and 37° C.

Induction of Expression Library. Competent cells were incubated with, ligation reactions, heat shocked, diluted 10-fold, and incubated at 30° C. for 1 hour. Cells were plated for single colonies and incubated at room temperature for 36 hours. Cells were washed from some of the plates with LB medium and a portion of the suspension was replated on TB agar and incubated at 30° C. for 18 hours followed by incubation at 37° C. for 10 hours or until average size colonies developed. A portion of the room temperature plate suspension was diluted in LB medium and grown at room temperature, and another portion diluted in TB and grown at 37° C. Both cultures were grown to saturation and served as the non-induced and induced liquid cultures. Cells from the room temperature and 37° C. plates were washed from the plates with 100 mM NaCl, washed with water, and portions dissolved in sample buffer prior to SDS-PAGE. These samples served as the non-induced and induced plate colonies. Portions of all sample pellets were frozen for later processing.

Falcon 96 well flat bottom plates (0.37 nil maximum volume) were used for small volume single colony inductions. TB (150 μL) was inoculated with single room temperature colonies and grown a 37° C. with shaking for 18 hours. From 1 to 1.5 μL of culture from each well was mixed, with an equal volume of 2× Laemmli loading buffer, heated for 5 minutes in boiling water, and applied to 14% Laemmli gels. The rest of the culture was used to isolate plasmid DNA.

Purification and Thrombin Digestion of Fusion Proteins. Frozen cell pellets were thawed and dissolved in 6M GuHCl, 500 mM NaCl, 20 mM Na Phosphate (pH 7.4), 2 mM 2-mercaptoethanol. Pellets from large scale inductions were first lysed (Giza and Huang 1989) and IBs isolated before dissolving in sample buffer. After centrifugation to remove particulate matter, the protein solutions were made to 10 mM imidazole and applied to a HiTrap Chelating HP column (Amersham Pharmacia Biotech) equilibrated with sample buffer. The column was washed with 10 volumes of 6 M Urea, 20 mM Tris HQ (pH 7.4), 500 mM NaCl, 2 mM 2-mercaptoethanol, 20 mM imidazole and bound proteins were eluted with the same buffer supplemented with 500 mM imidazole. Eluted proteins solutions were made to 50 mM 2-mercaptoethanol, 0.1% sarkosyl, incubated at 37° C. for 30 minutes and dialyzed against 2M urea, 20 mM Tris-HCl (pH 7.8), 50 mM NaCl, 1 mM 2-mercaptoethanol, 0.1% sarkosyl. Proteins were digested with thrombin for 5 hours at room temperature using 1 NIH unit per mg of protein. The small Rop moiety could be removed from the digest by passing the sample through the column after removal of the imidazole by dialysis.

Results

Example 1

Construction of Expression Plasmid pPGtrpRop$_{63}$

The plasmid pPGtrpRop$_{63}$ was derived from the expression plasmid pPGtrpRopAp (Giza and Huang 1989). pPGtrpRopAp was used to produce a number of proteins by the ligation of DMA sequences at the single PvuII site located in the 63 amino acid rop coding sequence. Interruption of the rop gene lead to the production of a fusion protein that was unable to control plasmid replication which resulted in cell lysis due to runaway plasmid replication. This lethal phenotype was suppressed by supplying functional Rop protein synthesized on a similar plasmid that co-existed in the cell. Upon loss of the helper plasmid, runaway plasmid replication occurred, followed by repressor titration of the trp promoter and induction of Rop fusion protein synthesis.

The need for the trans-helper plasmid was eliminated by ligating sequences at the 3' end of the 63 amino acid coding sequence as shown in FIG. 1. The 11.5 bp sequence ligated at the PvuII site of pPGtrpRopAp encodes the terminal 1.2 amino acids of rop, eliminates the original PvuII site in the rop gene while maintaining the correct amino acid sequence. The ligated sequence also encodes 6 histidine amino acids for protein purification, a thrombin protease cleavage sequence (LeuValProArg/GlyLeu) (SEQ ID NO:9), restriction cloning sites in 3 reading frames, and stop codons in 3 reading frames. No sequences were eliminated from the original vector.

Cells harboring pPGtrpRop$_{63}$ have a normal plasmid copy number when cultivated at room temperature (25° C.) and produce no novel protein bands when analyzed by SDS-PAGE. Media inoculated with frozen glycerol stocks, fresh overnight mom temperature cultures, or freshly transformed cells, followed by incubation at 37° C. for 18 to 24 hours produced a soluble protein at levels of 250 μg/ml of culture and plasmid DNA levels of 20-30 μg/ml This protein consists of 63 amino acids of native Rop fused to 23 amino acids contributed by the remainder of the inserted DNA sequence to yield a protein of 10.0 kDa.

Example 2

Construction of Fusion Plasmids with Defined Sequences

Eight fusion plasmids were constructed by ligating defined DNA sequences at the appropriate restriction site in the vector to produce gene fusions in the correct reading frames. Five of the constructs produced full-sized proteins: HIV-1 Integrase (IN), Green Fluorescent Protein (GFP), murine Survivin (Surv), HIV-1 Tat and hamster Metallothionein (MT). Smaller functional domains of 3 large proteins were produced: transcription factor Sp1 zinc finger domain, intercellular adhesion molecule-1, domain 1 (ICAM), and a portion of HIV-1 gp41 envelope protein spanning the 4-3 hydrophobic repeat region. In addition to these constructs high yielding rop fusions to the 72 amino acid "histone four helix bundle" of 2 thermophilic organisms were also produced, as we all as a construct consisting of multiple repeats of the 10 amino acid repeat motif of Abductin, a compressible elastomeric protein found in the hinge ligament of bivalve mollusks.

Growth at room temperature in LB medium resulted in little or no observable accumulation of novel protein bands when samples were analyzed by SDS-PAGE as shown in FIG. 2A. Even though the Rop protein is truncated in these structures, it is capable of controlling plasmid copy number at lower temperatures. The low copy number insures that the trp repressor proteins are not titrated by the trp promoter-operator sequences carried on the expression plasmids. Since sufficient copies of repressor are present in the cells, transcription is blocked on the expression plasmids and no fusion proteins are produced. Cultivation of bacteria at temperatures above 3° C. leads to loss of the ability to control plasmid replication: plasmid DNA accumulates to levels that greatly outnumber trp repressor molecules, and protein synthesis is automatically initiated.

FIG. 2B shows the results when 20 ml of Terrific Broth (TB) was inoculated with approximately 2 µL of frozen glycerol stocks and incubated, with shaking at 3° C. for 24 hours. No chemical inducers were added, and the culture temperature was not changed after inoculation. All lanes shown in FIGS. 2a and 2B show total bacterial proteins from $2.0 \times 10^7$ cells. The average $OD_{600}$ of the induced cultures was 7.1 and the average amount of culture volume applied to gels was 12 µL.

The amounts of fusion protein, produced by the 8 constructs shown in FIG. 2B were determined by making dilutions of the total bacterial proteins and comparing the bands to dilutions of a BSA standards run on the same gel. The average accumulation of fusions was 175 µg/mL with the highest being 460 and 330 µg/mL for ICAM and GFP respectively, and the lowest being 37 and 52 µg/ml for IN and Tat.

Even though high yields were produced using glycerol stocks as the inoculum, higher yields were realized when fresh room temperature cultures were used. FIG. 2C shows the results when a 500-fold dilution was made in the same medium and cultivated under the same conditions. To test the efficiency of the polyhistidine sequence at purifying the proteins, portions of the cultures were applied to a nickel affinity column, washed thoroughly, eluted from the column and assayed for protein yield. The average $OD_{600}$ was 11.4, and the average amount of protein eluted from the column was 340 µg when the proteins from 1 ml of induced cultures were applied to the column. The highest yielding construct was GFP at 1,300 µg because of an $OD_{600}$ of 18.7. The lowest yielding construct was MT at 71 µg. Larger scale inductions produced yields per ml of culture at the same levels as the smaller volume inductions. A glycerol stock of pRop$_{63}$Sp1$_{156}$ was used to inoculate 1.5 liters of TB. After an overnight incubation at 37° C. ($OD_{600}$ of 12.5), the cells were harvested and inclusion bodies (IBs) were isolated, washed extensively, and dissolved in guanidine-HCl (GuHCl). The yield of IBs before column, purification was 1.06 grams and 0.8 grams after purification.

Example 3

Construction of Expression Library Vectors pPGtrpRop BamHI A, B, C

The total proteins shown in the 9 lanes of FIG. 2B are total proteins from 9 to 24 µL of culture (average of 12 µL) and an average yield of 175 ng/µL. Since the fusion proteins could be easily distinguished from the host genomic proteins using less than 1 µL of culture, the feasibility of using this vector for high-throughput expression, library analysis was explored. The 3 blunt-end cloning sites in pPGtrpRop$_{63}$ was modified by inserting a BamHI site where DNA sequences could be inserted in 3 reading frames as shown in FIG. 1. The modified vector retained the 3 stop codons as well as the KpnI and PvuII sites that could be used for future modifications.

Figure 3:
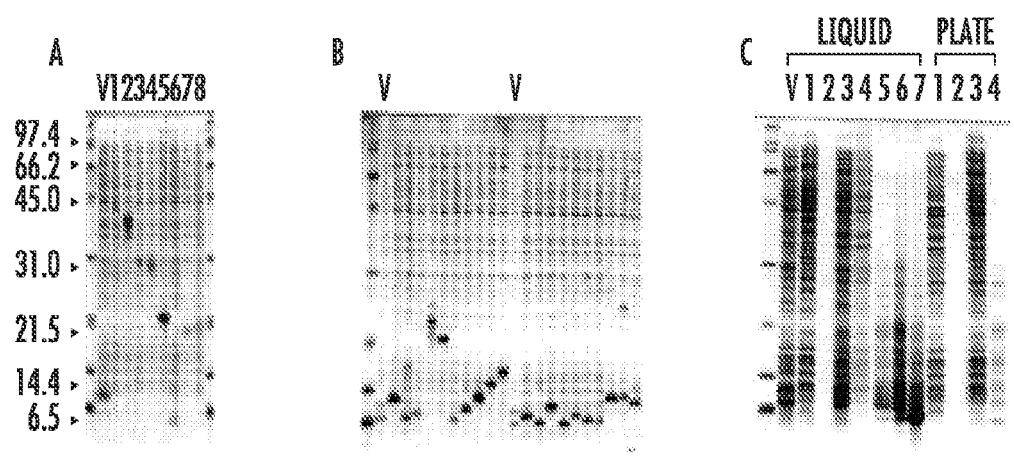
FIG. 3 shows a 14% SDS-PAGE analysis of expression of proteins cultivated in 96 well plates and as mixed bulk liquid cultures.

The initial test of the system was to determine if the 8 proteins shown in FIG. 2B could be cultivated under induced conditions, in very small volumes, inoculated with a single colony. Additionally, whether a few microliters of induced cultures show the fusion proteins without ambiguity on standard protein gels was also tested. FIG. 3A shows the results when 150 µL of TB in a 96 well plate (0.37 ml maximum volume wells) was inoculated with single colonies and incubated with shaking at 37° C. for 18 hours. The proteins shown in each lane were from 1.5 µL of culture that was mixed with 1.5 µL of 2× protein sample buffer. The mixture was boiled for 5 minutes, not centrifuged, and applied to the gel. Most of the fusion proteins are quite obvious except for IN and Tat in lanes 1 and 6 respectively.

These initial results led the present inventors to explore the other important factor in determining the suitability of this plasmid for library construction. The present inventors wanted to determine the percentage of constructs that resulted in obvious bands on gels when random DNA fragments were ligated to the 3 reading frame vectors.

The host bacteria HB101 was digested with the restriction enzyme Sau3AI and DNA fragments from 100 to 400 bp were isolated from agarose gels. Ligations and transformations yielded about 5000 colonies from each vector when grown on 25×25 cm plates. Colonies were inoculated as before and 50 wells of each reading frame vector were analyzed on protein gels. Strong, obvious bands were observed in 96% of the samples with molecular weights in the range consistent with the size of the ligated fragments. The ligations were repeated with DNA fragments ranging from 300 to 600 bp and analyzed 25 inductions of each vector. FIG. 3B shows typical results when 1.5 µL of culture (vector A) was applied to SDS gels. The average size of the DNA inserts was 500 bp and all randomly picked samples in FIG. 3B had inserts.

To analyze the total population of proteins produced, cells were stripped from plates and grown in bulk at room temperature followed by induction growth (500-fold dilution) at 37° C. for 24 hours. To analyze single colony protein inductions, room temperature bulk cultures were plated on rich agar, and incubated at room temperature. One set of plates was kept at room temperature as a non-induced control, and the other set was incubated at 37° C. for 18 hours. Colonies (~1500) were stripped from plates and dissolved in buffer containing 6 M GuHCl. Portions of liquid cultures were centrifuged and dissolved in the same buffer. These samples were applied to a nickel affinity column to determine the amount and size range of the fusion proteins.

The results of the liquid and plate inductions are shown in FIG. 3C. All lanes contain proteins from $1.5 \times 10^7$ cells except lanes 6, 7, and Plate lane 4, which contain $6.0 \times 10^7$ cells. Lane V shows total proteins from cells harboring the expression vector without insert, grown under induced conditions (37° C.). This protein often migrates as a doublet. Analysis of the column purified room temperature (non-induced) samples in lanes 2 (liquid and Plate) show a trace of bound proteins indicating that growth in culture or on plates produced no significant protein accumulation whereas growth under induced conditions (37° C.) in lanes 5, 6, and Plate lane 4 show very obvious protein bands ranging in size from 10 to 30 kDa. This is the molecular weight range expected for the size of the DNA fragments ligated to the vector and fusion protein synthesis terminated by stop codons carried on the fragments or terminated by stop codons supplied by the vector. After thrombin digestion of the proteins shown in lanes 6, we see a shift in molecular weight (lane 7) consistent with the loss of mass contributed by the Rop moiety.

Protein analysis of the column eluates yielded values 350 µg/mL of induced culture and 880 µg from the stripped plate. On a per cell basis the induce culture yield was approximately 8-fold greater than the induced plate yield. Protein analysis of the room temperature plate and culture column eluates showed barely detectable levels of protein (lanes 2).

This expression plasmid not only produces high levels of protein but also generates high levels of plasmid DNA, ranging from about 0.25 to about 5 µg per microliter plate well (average of 1.5 µg). These amounts of DNA were sufficient to determine insert size as well as providing enough plasmid for several restriction digests. Because the protein size could be quickly correlated with the size of the DNA insert, the present inventors were able to obtain some information about the pool, of fusion proteins. About 60% of the proteins produced by the shot-gun ligations were terminated by stop codons on the ligated DNA fragments, while the remainder were terminated by stop codons supplied by the vector.

We claim:

1. An expression vector for use in *E. coli* comprising a nucleic acid sequence encoding (a) a tryptophan (trp) promoter-operator; (b) a repressor of primer (Rop) promoter and Rop gene downstream from the trp promoter-operator; (c) a purification tag sequence and a protease cleavage site downstream of the Rop promoter and Rop gene; and (d) a multiple cloning site downstream of the protease cleavage site.

2. The expression vector of claim 1, wherein the purification tag sequence is a polyhistidine tag sequence.

3. The expression vector of claim 1, wherein the Rop gene encodes the amino acid sequence of SEQ ID NO:12.

4. The expression vector of claim 1, wherein the Rop gene encodes a polypeptide having at least 95% identity to SEQ ID NO:12.

5. The expression vector of claim 1, wherein the protease is thrombin.

6. An *E. coli* cell comprising the expression vector of claim 1.

7. A kit comprising the expression vector of claim 1.

8. A recombinant expression vector for use in *E. coli* comprising a nucleic acid sequence encoding (a) a tryptophan (trp) promoter-operator; (b) a repressor of primer (Rop) promoter and Rop gene downstream from the trp promoter-operator; (c) a polyhistidine tag sequence and a thrombin cleavage site downstream of the Rop promoter and Rop gene; and (d) a multiple cloning site downstream of the protease cleavage site.

9. The expression vector of claim 6, wherein the Rop gene encodes the amino acid sequence of SEQ ID NO:12.

10. The expression vector of claim 8, wherein the Rop gene encodes a polypeptide having at least 95% identity to SEQ ID NO:12.

11. A plasmid designated pPGtrpRop$_{63}$(ATCC Designation No. PTA-122515).

12. An *E. coli* cell line comprising the plasmid of claim 11.

13. A kit comprising the plasmid of claim 11.

14. A plasmid designated pPGtrpRop$_{63}$BamHI A (ATCC Designation No. PTA-122516).

15. A plasmid designated pPGtrpRop$_{63}$BamHI B (ATCC Designation No. PTA-122517).

16. A plasmid designated pPGtrpRop$_{63}$BamHI C (ATCC Designation No. PTA-122514).

17. An expression vector for use in *E. coli* comprising (a) a repressor of primer (Rop) gene operatively linked to a tryptophan (trp) promoter-operator; (b) a purification tag sequence and a protease cleavage site downstream of the Rop gene; and (d) a multiple cloning site downstream of the protease cleavage site, wherein the insertion of a heterologous gene of interest into the multiple cloning site and subsequent expression thereof in a host cell produces a fusion protein comprising the Rop protein and the protein encoded by the heterologous gene of interest without the need of chemical inducers, temperature shifts, or growth medium alterations to initiate protein synthesis, and wherein the fusion protein controls plasmid replication at temperatures below about 30° C. but exhibits runaway plasmid replication when cultured at about 37° C.

* * * * *

SEQUENCE LISTING

```
<160> NUMBER OF SEQ ID NOS: 12

<210> SEQ ID NO 1
<211> LENGTH: 40
<212> TYPE: PRT
<213> ORGANISM: Artificial Sequence
<220> FEATURE:
<223> OTHER INFORMATION: Insert sequence for pPGtrpRop63 comprising
      c-terminal portion of Rop protein, purification tag sequence,
      protease cleavage site, and multiple cloning site

<400> SEQUENCE: 1

Leu Tyr Arg Ser Cys Leu Ala Arg Phe Gly Asp Asp Gly Glu Asn Leu
1               5                   10                  15

Arg Ser His His His His His His Arg Ser Leu Val Pro Arg Gly Thr
            20                  25                  30

Pro Gly Ile Ser Ala Asp Leu Asp
        35                  40

<210> SEQ ID NO 2
<211> LENGTH: 135
<212> TYPE: DNA
<213> ORGANISM: Artificial Sequence
<220> FEATURE:
<223> OTHER INFORMATION: Insert sequence for pPGtrpRop63 encoding
      c-terminal portion of Rop protein, purification tag sequence,
      protease cleavage site, and multiple cloning site

<400> SEQUENCE: 2
ctttaccgca gttgtctcgc acgtttcggg gatgacggtg aaaacctcag atcccaccat      60
caccatcacc atagatctct ggttccgcgt ggtaccccg ggatatcagc tgatctagat     120
tagtatctgc ctcgc                                                     135

<210> SEQ ID NO 3
<211> LENGTH: 15
<212> TYPE: DNA
<213> ORGANISM: Artificial Sequence
<220> FEATURE:
<223> OTHER INFORMATION: Modification of KpnI and PvuII site to produce
      SmaI and BamHI site

<400> SEQUENCE: 3
ccccggggga tccag                                                      15

<210> SEQ ID NO 4
<211> LENGTH: 19
<212> TYPE: DNA
<213> ORGANISM: Artificial Sequence
<220> FEATURE:
<223> OTHER INFORMATION: Modification of KpnI and PvuII site to produce
      SmaI and BamHI site

<400> SEQUENCE: 4 catggggggcc ccctaggtc                                                 19
```

<210> SEQ ID NO 5
<211> LENGTH: 14
<212> TYPE: DNA
<213> ORGANISM: Artificial Sequence
<220> FEATURE:
<223> OTHER INFORMATION: Modification of KpnI and PvuII site to produce
      SmaI and BamHI site

<400> SEQUENCE: 5
ccccggggat ccag                                                        14

<210> SEQ ID NO 6
<211> LENGTH: 18
<212> TYPE: DNA
<213> ORGANISM: Artificial Sequence
<220> FEATURE:
<223> OTHER INFORMATION: Modification of KpnI and PvuII site to produce
      SmaI and BamHI site

<400> SEQUENCE: 6 catggggggcc cctaggtc                                                   18

<210> SEQ ID NO 7
<211> LENGTH: 13
<212> TYPE: DNA
<213> ORGANISM: Artificial Sequence
<220> FEATURE:
<223> OTHER INFORMATION: Modification of KpnI and PvuII site to produce
      SmaI and BamHI site

<400> SEQUENCE: 7
ccccgggatc cag                                                         13

<210> SEQ ID NO 8
<211> LENGTH: 17
<212> TYPE: DNA
<213> ORGANISM: Artificial Sequence
<220> FEATURE:
<223> OTHER INFORMATION: Modification of KpnI and PvuII site to produce
      SmaI and BamHI site

<400> SEQUENCE: 8 catggggggcc ctaggtc                                                    17

<210> SEQ ID NO 9
<211> LENGTH: 6
<212> TYPE: PRT
<213> ORGANISM: Artificial Sequence
<220> FEATURE:
<223> OTHER INFORMATION: Thrombin cleavage site

<400> SEQUENCE: 9

Leu Val Pro Arg Gly Thr
1               5

<210> SEQ ID NO 10
<211> LENGTH: 30
<212> TYPE: DNA
<213> ORGANISM: Artificial Sequence
<220> FEATURE:
<223> OTHER INFORMATION: 5' primer used to generate a PCR product from
      pcDNA3.1-myc-His that encodes the entire murine Survivin gene with
      XmaI restriction site termini

<400> SEQUENCE: 10
catcccggga tgggagctcc ggcgctgccc                                       30

```
<210> SEQ ID NO 11
<211> LENGTH: 33
<212> TYPE: DNA
<213> ORGANISM: Artificial Sequence
<220> FEATURE:
<223> OTHER INFORMATION: 3' primer used to generate a PCR product from
      pcDNA3.1-myc-His that encodes the entire murine Survivin gene with
      XmaI restriction site termini

<400> SEQUENCE: 11
taccccgggt taggcagcca gctgctcaat tga                                   33

<210> SEQ ID NO 12
<211> LENGTH: 63
<212> TYPE: PRT
<213> ORGANISM: Escherichia coli
<220> FEATURE:
<221> NAME/KEY: MISC_FEATURE
<222> LOCATION: (1)..(63)
<223> OTHER INFORMATION: Amino acid sequence of regulatory protein Rop
      from E. Coli

<400> SEQUENCE: 12

Met Thr Lys Gln Glu Lys Thr Ala Leu Asn Met Ala Arg Phe Ile Arg
1               5                  10                  15

Ser Gln Thr Leu Thr Leu Leu Glu Lys Leu Asn Glu Leu Asp Ala Asp
            20                  25                  30

Glu Gln Ala Asp Ile Cys Glu Ser Leu His Asp His Ala Asp Glu Leu
        35                  40                  45

Tyr Arg Ser Cys Leu Ala Arg Phe Gly Asp Asp Gly Glu Asn Leu
    50                  55                  60
```